United States Patent
Hübner

(10) Patent No.: US 10,820,811 B2
(45) Date of Patent: Nov. 3, 2020

(54) APPARATUS FOR DETERMINING BLOOD PRESSURE

(71) Applicant: PREVENTICUS GMBH, Jena (DE)

(72) Inventor: Thomas Hübner, Jena (DE)

(73) Assignee: PREVENTICUS GMBH, Jena (DE)

( * ) Notice: Subject to any disclaimer, the term of this patent is extended or adjusted under 35 U.S.C. 154(b) by 214 days.

(21) Appl. No.: 15/552,673

(22) PCT Filed: Feb. 24, 2016

(86) PCT No.: PCT/EP2016/053878
§ 371 (c)(1),
(2) Date: Aug. 22, 2017

(87) PCT Pub. No.: WO2016/135202
PCT Pub. Date: Sep. 1, 2016

(65) Prior Publication Data
US 2018/0214037 A1      Aug. 2, 2018

(30) Foreign Application Priority Data
Feb. 27, 2015   (EP) .................................... 15157059

(51) Int. Cl.
*A61B 5/02* (2006.01)
*A61B 5/021* (2006.01)
(Continued)

(52) U.S. Cl.
CPC ........ *A61B 5/02108* (2013.01); *A61B 5/0295* (2013.01); *A61B 5/7225* (2013.01);
(Continued)

(58) Field of Classification Search
CPC . A61B 5/02108; A61B 5/7225; A61B 5/0295; A61B 5/7275; A61B 5/0255; A61B 5/7203; A61B 5/6898; A61B 5/02125
See application file for complete search history.

(56) References Cited

U.S. PATENT DOCUMENTS

2010/0317976 A1* 12/2010 Chelma .................... A61B 5/02
                                                    600/485
2012/0277600 A1* 11/2012 Greenhut ........... A61B 5/02108
                                                    600/485
(Continued)

FOREIGN PATENT DOCUMENTS

WO        2014022906 A1     2/2014

OTHER PUBLICATIONS

Zhao, Y., and W. H. Kullmann. "Determining Blood Pressure Changes and Vascular Stiffness State Using Optical Pulse Pressure Analysis." Biomedical Engineering/Biomedizinische Technik (2013) (Year: 2013).*

(Continued)

*Primary Examiner* — Navin Natnithithadha
*Assistant Examiner* — Andrey Shostak
(74) *Attorney, Agent, or Firm* — Fish & Richardson P.C.

(57) ABSTRACT

An apparatus for determining blood pressure has a control unit and a device for providing pulse wave data representative of a heartbeat of a human subject. The subject has a body height, an age, and a gender. The control unit is configured for receiving the pulse wave data, selecting a portion of the pulse wave data indicative of one or more heart periods, and, for each respective heart period of the one or more heart periods, determining a systolic component of the respective heart period, approximating the systolic component with a first Gaussian function and a second Gaussian function, and determining a time difference between the first and second Gaussian functions. The blood pressure value of the subject is determined based on the time difference, the body height, and the age.

23 Claims, 5 Drawing Sheets

(51) Int. Cl.
 A61B 5/0295 (2006.01)
 A61B 5/00 (2006.01)
 A61B 5/0255 (2006.01)
(52) U.S. Cl.
 CPC ......... *A61B 5/0255* (2013.01); *A61B 5/02125* (2013.01); *A61B 5/6898* (2013.01); *A61B 5/7203* (2013.01); *A61B 5/7275* (2013.01)

(56) References Cited

U.S. PATENT DOCUMENTS

| | | | | |
|---|---|---|---|---|
| 2013/0150736 A1* | 6/2013 | Romano | ............ | A61B 5/02108 600/485 |
| 2013/0184596 A1 | 7/2013 | Fujii et al. | | |
| 2014/0249424 A1* | 9/2014 | Fan | ...................... | A61B 5/0255 600/473 |
| 2015/0182132 A1* | 7/2015 | Harris | .................. | A61B 5/0295 340/870.01 |
| 2017/0281050 A1* | 10/2017 | Noguchi | .................. | A61B 5/08 |
| 2018/0199893 A1* | 7/2018 | Hubner | ................ | A61B 5/7282 |

OTHER PUBLICATIONS

Gaussian Models, MATLAB & Simulink, https://www.mathworks.com/help/curvefit/gaussian.html (Year: 2019).*

GraphPad Curve Fitting Guide, https://www.graphpad.com/guides/prism/7/curve-fitting/reg_how_to_gaussian.htm?toc=0&printWindow (Year: 2019).*

Zhao, Y. et al., "Determining Blood Pressure Changes and Vascular Stiffness State Using Optical Pulse Pressure Analysis," Biomedical Engineering., 2013.

Zhao, Y. et al., "Applanation Tonometry for Determining Arterial Stiffness," Biomedical Engineering, 2012, pp. 669-672, vol. 57.

Elgendi, Mohamed et al., "On the Analysis of Fingertip Photoplethysmogram Signals," Current Cardiology Reviews, 2012, pp. 14-25, vol. 8, No. 1.

Scully, Christopher G. et al., "Physiological Parameter Monitoring from Optical Recordings With a Mobile Phone," IEEE Transactions on Biomedical Engineering, IEEE Service Center, 2012, pp. 303-306, vol. 59, No. 2.

Ahimastos, Anna A., "Gender Differences in Large Artery Stiffness Pre- and Post Puberty," The Journal of Clinical Endocrinology & Metabolism, 2003, pp. 5375-5380, vol. 88, No. 11.

Primatesta, Paola et al., "Association Between Smoking and Blood Pressure Evidence From the Health Survey for England," Scientific Contributions, 2001, pp. 187-194.

Apr. 22, 2016 International Search Report issued in International Patent Application No. PCT/EP2016/053878.

Apr. 22, 2016 Written Opinion issued in International Patent Application No. PCT/EP2016/053878.

Chowienczyk Phillip J et al., "Photoplethysmographic Assessment of Pulse Wave Reflection," Journal of the American College of Cardiology, vol. 34, No. 7, 1999.

Laurent, Stephane, et al., "Aortic Stiffness Is an Independent Predictor of All-Cause and Cardiovascular Mortality in Hypertensive Patients," Hypertension 2001, vol. 37, pp. 1236-1241.

O'Rourke, Michael et al., "Pulse wave analysis," Research Methods in Human Cardiovascular Phamacology, Blackwell Science Ltd. vol. 51, pp. 507-522.

Millasseau, S.C., "Determination of age-related increases in large artery stiffness by digital pulse contour analysis," Clinical Science 2002, vol. 103, pp. 371-377.

Hayward, Christopher et al., "Assessment of Endotheilial Function Using Peripheral Waveform Analysis," Journal of America College of Cardiology, vol. 40, No. 3, 2002.

Padilla, Juan et al., "Pulse Wave Velocity and Digital Volume Pulse as Indirect Estimators of Blodd Pressure: Pilot Study on Healthy Volunteers," Cardiovasc Eng, Springer Science +Business media LLC, 2009.

\* cited by examiner

APPARATUS FOR DETERMINING BLOOD PRESSURE

TECHNICAL FIELD

The present invention relates to an apparatus and noninvasive method for determining the blood pressure of a human subject. Blood pressure is determined based on pulse waveform analysis.

BACKGROUND ART

Blood pressure is the pressure exerted by circulating blood upon the walls of blood vessels and is one of the principal vital signs of a person. It is regulated by the nervous and endocrine systems and varies depending on a number of factors including current activity and general health condition of a person. Pathologically low blood pressure is referred to as hypotension, and pathologically high blood pressure is referred to as hypertension. Both pathologies can have different causes and can range from mild to severe, with both acute and chronic forms. Chronic hypertension is a risk factor for many complications, including peripheral vascular disease, heart attack, and stroke. Both hypertension and hypotension are often undetected for longer periods of time because of infrequent monitoring.

Hypertension is generally more common and constitutes the predominant risk factor for a cardiovascular disease and associated health problems including death, higher than those for smoking and diabetes. One major problem with hypertension is that high blood pressure does not necessarily entail pronounced symptoms and that, consequently, there are many people living their lives without realizing that they have elevated or high blood pressure. Measuring and monitoring blood pressure can be done in a number of ways, including at home, as an outpatient, or as an inpatient. However, sporadic and/or infrequent measurements are typically not meaningful enough for effective early detection of hypertension and associated diseases, due to the intervals between measurements often being too long and the measurements being done not often enough.

Medical professionals commonly measure arterial pressure using a sphygmomanometer, which historically used the height of a column of mercury to reflect the circulating pressure, and blood pressure values are typically reported in millimeters of mercury (mm Hg). For each heartbeat, blood pressure varies between systolic and diastolic pressures. Systolic pressure is the peak pressure in the arteries, occurring near the end of a cardiac cycle when the ventricles are contracting. Diastolic pressure is the minimum pressure in the arteries, occurring near the beginning of a cardiac cycle when the ventricles are filled with blood. Typical normal measured values for a resting and healthy adult are 120 mm Hg systolic pressure and 80 mm Hg diastolic pressure (i.e. 120/80 mm Hg).

Systolic and diastolic arterial blood pressures are not static but undergo natural variations from one heartbeat to the next and throughout the day (in a circadian rhythm). Variations occur in response to stress or exercise, changes in nutrition, and disease or associated medication. Blood pressure is one of the four main vital signs, further including body temperature, respiratory rate, and pulse rate, that are routinely monitored by medical professionals and healthcare providers.

Blood pressure can be measured in a noninvasive manner, including palpation, auscultatory or oscillometric methods, continuous noninvasive techniques (CNAP), and based on the pulse wave velocity (PWV) principle. Measuring blood pressure invasively, for example using intravascular cannulae, can produce very accurate measurements, but is much less common due to its invasive nature and is typically restricted to inpatient treatment.

Blood pressure in humans is significantly affected by the elasticity of the vascular system. The elasticity of the vascular system of a person depends on different factors including age, but also on the presence or absence of particular diseases or illnesses. If, for example, the elasticity of the vascular system of a patient decreases due to old age or due to the patient suffering from arteriosclerosis, the blood pressure of the patient increases.

A measure for arterial stiffness is the arterial stiffness index (SI) that can be recorded photoplethysmographically as has been described by P. J. Chowienczyk, R. P. Kelly, H. MacCallum, S. C. Millasseau, T. L. G. Andersson, R. G. Gosling, J. M. Ritter, and E. E. Änggård in "Photoplethysmographic assessment of pulse wave reflection: Blunted response to endothelium-dependent beta2-adrenergic vasodilation in type II diabetes mellitus," J. Am. Coll. Cardiol., vol. 34, pp. 2007-2014, 1999, and by C. S. Hayward, M. Kraidly, C. M. Webb, and P. Collins in "Assessment of endothelial function using peripheral waveform analysis: A clinical application," J. Am. Coll. Cardiol., vol. 40, pp. 521-528, 2002.

The stiffness index is a measure of the loss of elasticity in the arteries that occurs with onset of vascular disease and advancing age. One way to calculate the stiffness index is to detect two significant points within a pulse period. The first point denotes the maximum amplitude of the systolic portion of the graph, which is caused by the expulsion of blood from the heart and by the direct propagation of the pulse wave through the vascular system, for example into extremities such as the fingers. At the same time, this pulse wave is reflected at each branch of the vascular system and where the diameter of a vessel changes. Due to this reflection of the pulse wave, a secondary (delayed) component is created, the maximum of which is also used in calculating the stiffness index. The second point, thus, denotes the maximum amplitude of the reflected pulse wave. The stiffness index is then calculated as the relationship of the body height of the patient and the time difference between the occurrence of the first point (i.e. the maximum of the pulse wave) and the second point (i.e. the maximum of the reflected pulse wave) in the graph, also referred to as peak-to-peak time (PPT).

S. C. Millasseau, R. P. Kelly, J. M. Ritter, and P. J. Chowienczyk, in "Determination of age-related increases in large artery stiffness by digital pulse contour analysis.," Clin. Sci. (Lond)., vol. 103, pp. 371-377, 2002, have found in a study on 87 subjects (ages 21-68, 29 female), that the stiffness index had a good correlation of $r=0.65$ with the PWV, which is an established measure of vascular stiffness. The importance of the PWV as an independent predictor for elevated cardiovascular mortality has been shown by S. Laurent, P. Boutouyrie, R. Asmar, I. Gautier, B. Laloux, L. Guize, P. Ducimetiere, and A. Benetos, in "Aortic stiffness is an independent predictor of all-cause and cardiovascular mortality in hypertensive patients.," Hypertension, vol. 37, pp. 1236-1241, 2001. The distance between the two peaks decreases over time (i.e. age), resulting in an increased in stiffness index with old age. Further, the stiffness index depends on the blood pressure, which has been verified in the same study. A univariate analysis showed a significant correlation of the stiffness index with age ($r=0.67$), with systolic pressure ($r=0.32$), with diastolic pressure ($r=0.48$), and mean arterial pressure (MAP, $r=0.45$). Multiple regressions using the factors age and MAP resulted in values of r=0.69. These dependencies occurred in the same manner for the PWV, further confirming that the stiffness index contains data similar to the PWV. Moreover, a similar behavior of the stiffness index was verified in connection with administration of vasoactive substances. The relevance of the stiffness index as a measure of vascular elasticity has, thus, been proven.

An aim of the present invention is to provide an apparatus and non-invasive method for determining the blood pressure of a human subject easily and efficiently. It is a further aim to provide an apparatus and non-invasive method for determining the blood pressure of a human with an improved accuracy.

A further aim of the present invention is to provide an apparatus for performing the non-invasive method for determining the blood pressure of a human subject. In particular, the apparatus is a mobile device, and preferably a conventional smart phone provided with a light source and an optical sensor.

SUMMARY OF INVENTION

According to the invention, in a $1^{st}$ aspect there is provided an apparatus for determining blood pressure, comprising a control unit; and a means for providing pulse wave data representative of a heart beat of a human subject, the subject having a body height, an age, and a gender; wherein the control unit is configured to perform the steps of: receiving the pulse wave data; selecting a portion of the pulse wave data indicative of one or more heart periods; for each/at least one respective heart period of the one or more heart periods: —determining a systolic component of the respective heart period; —approximating the systolic component with a first Gaussian function and a second Gaussian function; and—determining a time difference between the first and second Gaussian functions; the control unit being further configured for determining a blood pressure value of the subject based on the time difference, the body height, and/or the age.

According to a $2^{nd}$ aspect in accordance with the $1^{st}$ aspect, the step of determining the blood pressure value comprises determining a preliminary stiffness index based on the body height and the time difference; determining an adjusted stiffness index based on the preliminary stiffness index and the age; and determining the blood pressure value based on the adjusted stiffness index and a regression model.

According to a $3^{rd}$ aspect in accordance with any one of the preceding aspects, the portion of the pulse wave data is indicative of a plurality of heart periods, and wherein the step of determining the time difference further comprises determining the time difference for the plurality of successive heart periods as an average value based on the respective time differences determined for the plurality of heart periods.

According to a $4^{th}$ aspect in accordance with the preceding aspect, the average value is the median value of the determined respective time differences.

According to a $5^{th}$ aspect in accordance with any one of the preceding aspects, the first and second Gaussian functions have a respective maximum amplitude, the maximum amplitude of the first Gaussian function being greater than or equal to the maximum amplitude of the second Gaussian function.

According to a $6^{th}$ aspect in accordance with any one of the preceding aspects, the first and second Gaussian functions have respective first and second standard deviations, the first and second standard deviations being equal to each other.

According to a $7^{th}$ aspect in accordance with any one of the preceding aspects, the step of approximating the systolic component comprises fitting the first and second Gaussian functions to the systolic component using $$F(a,b,c,d,f) = \sum_{i=1}^{N}\left(S_i - \left(a\cdot e^{-\frac{1}{2}\left(\frac{t-b}{c}\right)^2} + d\cdot e^{-\frac{1}{2}\left(\frac{t-f}{c}\right)^2}\right)\right)^2 \overset{!}{=} \min$$

with a, b, c, d, and f being determined using non-linear optimization or curve-fitting.

According to an $8^{th}$ aspect in accordance with any one of aspects 2 to 7, the regression model comprises a regression function $$f(SI_a, g) = BP_{sys},$$

where $SI_a$ is the adjusted stiffness index, g is the gender of the subject, and $BP_{sys}$ is the blood pressure; and wherein determining the blood pressure value comprises determining the blood pressure value based on the regression function.

According to a $9^{th}$ aspect in accordance with the preceding aspect, the regression function comprises a linear function of the type $$f(x) = ax + b,$$

wherein a ranges from 1 to 20 mmHg/(m/s) and b ranges from 0 to 80 mmHg, more preferably wherein a ranges from 5 to 15 mmHg/(m/s) and b ranges from 20 to 60 mmHg.

According to a $10^{th}$ aspect in accordance with any one of aspects 2 to 9, determining the adjusted stiffness index ($SI_a$) is based on an adjustment function $$f(SI_p) = SI_a$$

where $SI_p$ is the preliminary stiffness index and $SI_a$ is the adjusted stiffness index.

According to an $11^{th}$ aspect in accordance with the preceding aspect, the adjustment function is a linear function of the type $$f(x) = cx + d,$$

where c and d are adjustment factors determined based on a plurality of value pairs comprising an age value and an associated stiffness index value; optionally wherein:

$$C = \frac{SI - \mu}{\text{range(age)}}$$

with µ=0.109*age+3.699 and range(age)=0.1663*age+4.3858−µ,
age being the age of the subject, and
d=0.

According to a $12^{th}$ aspect in accordance with any one of the preceding aspects, determining the systolic component comprises determining a respective global maximum of the respective heart period; determining the second order derivative of the respective heart period; determining a maximum value of the second order derivative located at least at a predetermined time difference from the global maximum; and defining the systolic component as a portion of the heart period between the start of the heart period and the maximum value.

According to a 13th aspect in accordance with the preceding aspect, the predetermined time difference to the global maximum is 350 ms or less, preferably wherein the predetermined time difference to the global maximum is 250 ms or less.

According to a 14th aspect in accordance with any one of aspects 2 to 13, determining the preliminary stiffness index is based on a function $$SI_p = \frac{h}{WWT},$$

where h is the subject height, WWT is the time difference, and $SI_p$ is the preliminary stiffness index.

According to a 15th aspect in accordance with any one of the preceding aspects, the apparatus further comprises a light source configured for transmitting light into an extremity of a subject; wherein the means for providing pulse wave data comprises an optical sensor configured for receiving light reflected from blood flow through the extremity.

According to a 16th aspect in accordance with the preceding aspect, the step of receiving the pulse wave data comprises activating the light source and receiving the pulse wave data based on a signal provided by the optical sensor.

According to a 17th aspect in accordance with the preceding aspect, the optical sensor comprises a video sensor, and wherein the step of receiving the pulse wave data further comprises receiving a video stream indicative of the reflected light based on the signal; selecting a region of interest from the video stream containing a plurality of pixels, the region of interest optionally having a size of 50×50 pixels; selecting a plurality of frames from the video stream, each frame of the plurality of frames having a respective time stamp; for each respective frame: —determining, within the region of interest, a first sample value indicative of the sum of the values of a green subcomponent of each pixel of the plurality of pixels; —associating each first sample with the respective time stamp; —generating a first pulse wave from the first samples; and the step of receiving the pulse wave data further comprising determining a second pulse wave by re-sampling the first pulse wave based on the respective time stamps.

According to an 18th aspect in accordance with the preceding aspect, determining the second pulse wave further comprises filtering the second pulse wave using a bandpass filter, the bandpass filter optionally removing all frequencies not falling within a range from 0.6 Hz to 2.5 Hz.

According to a 19th aspect in accordance with any one of the preceding aspects, the portion of the pulse wave data is indicative of 1 to 50 heart periods, preferably wherein the portion of the pulse wave data is indicative of 1 to 40 heart periods, more preferably wherein the portion of the pulse wave data is indicative of 10 to 30 heart periods.

According to a 20th aspect in accordance with any one of the preceding aspects, the portion of the pulse wave data is indicative of a plurality of successive heart periods.

According to a 21st aspect in accordance with any one of aspects 15 to 20, the sensor is an optical sensor and the apparatus further comprises a light source, the sensor being configured to detect a signal emitted by the light source and reflected by part of a body of the subject, optionally the part of the body of the subject comprising a pulsatile blood flow of the subject.

According to a 22nd aspect in accordance with any one of the preceding aspects, the apparatus further comprises input means configured to receive a user input initiating determining of the blood pressure value.

According to a 23rd aspect in accordance with any one of the preceding aspects, the apparatus further comprises output means configured to display the blood pressure value.

According to a 24th aspect in accordance with any one of the preceding aspects, the means for providing pulse wave data comprises a memory unit configured to store the pulse wave data.

Advantages of the apparatus for determining the blood pressure include that the blood pressure can be determined with improved accuracy.

DETAILED DESCRIPTION

Figure 1:
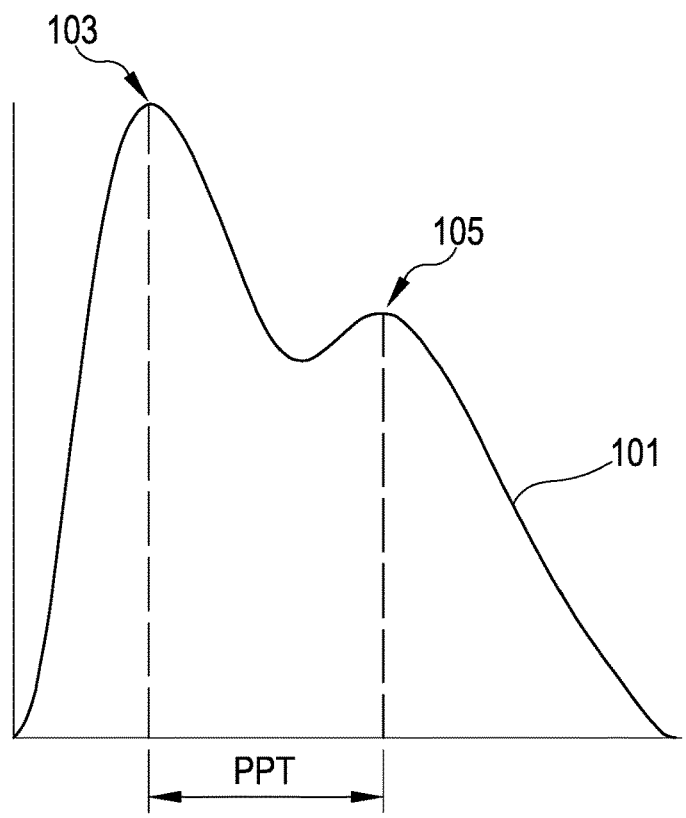
FIG. 1 illustrates how the stiffness index is determined in accordance with prior art methods.

FIG. 1 illustrates how the stiffness index is determined in accordance with prior art methods. The diagram in FIG. 1 shows a pulse wave signal 101 over time t. As shown, the stiffness index is determined based on the inflection points of the graph, in particular, those on the falling edge thereof. Based on the inflection points, the graph is partitioned in respective segments so that the systolic peak 103 and the diastolic peak 105 can be determined. The PPT is defined as the time between maximum 103 and maximum 105. Subsequently, given the subject height h (in m) and the PPT (in s) the SI can be calculated as:

$$SI = \frac{h}{PPT}$$

The first peak 103 used to determine the PPT corresponds the maximum of the original pulse wave, which can usually be determined with sufficient accuracy. The second peak 105, however, is typically affected by the closing of the heart valves and suffers from a superposition of the original pulse wave and the reflected pulse wave, both of which are shown in superposition as pulse wave 101. Hence, the position of the second peak 105 does not necessarily correspond to the position of the reflected pulse wave with high accuracy, but, on the contrary, entails a substantial margin of error. Therefore, determining the stiffness index based on the first and second peaks 103 and 105 using the PPT is at least limited to the level of correspondence between the position of the second peak 105 and the actual position of the reflected pulse wave. As a result, the accuracy of the stiffness index determined based on the PPT can be improved.

Figure 2:
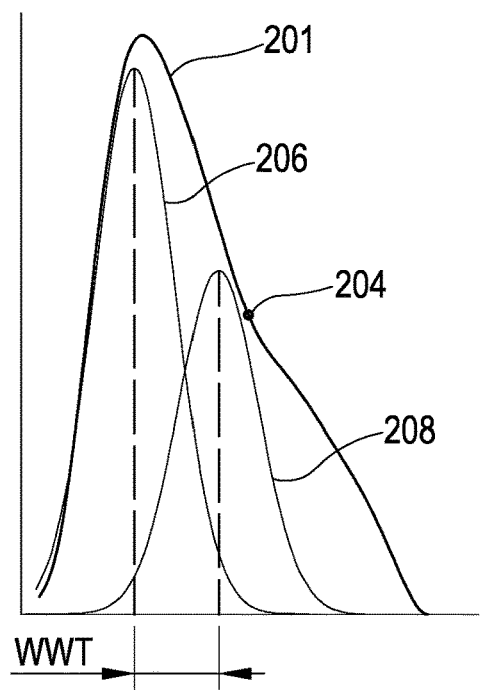
FIG. 2 illustrates how the stiffness index is determined in accordance with the present invention.

FIG. 2 illustrates how the stiffness index is determined in accordance with the present invention. The diagram in FIG. 2 shows a pulse wave signal 201 over time t as well as corresponding wave components 206 and 208 of the original pulse wave and the wave reflected mainly by the aortic bifurcation. FIG. 2 also shows an inflection point 204. With respect to what is shown in FIG. 1 it is noted that a simple partitioning based on the inflection points does not necessarily correspond to the actual physiological wave components because of the reasons set forth in the previous paragraph. In contrast, in accordance with the present invention, the actual original pulse wave and the wave reflected by the aortic bifurcation are determined by approximation of the graph with Gaussian functions, by which the two component waves $w_{original}$ 206 and $w_{reflected}$ 208 can be obtained with very high accuracy. Here, the time difference is determined as the time difference between the component waves $w_{original}$ and $w_{reflected}$ as opposed to the time difference between two maxima of the graph. This facilitates determining, instead of a PPT, a wave-to-wave time (WWT), which corresponds to the actual time difference between the original pulse wave and the reflected pulse wave with a substantially higher level of accuracy. This, in turn, facilitates a more accurate calculation of the SI and, thus, leads to an improved correlation with the blood pressure.

Figure 3:
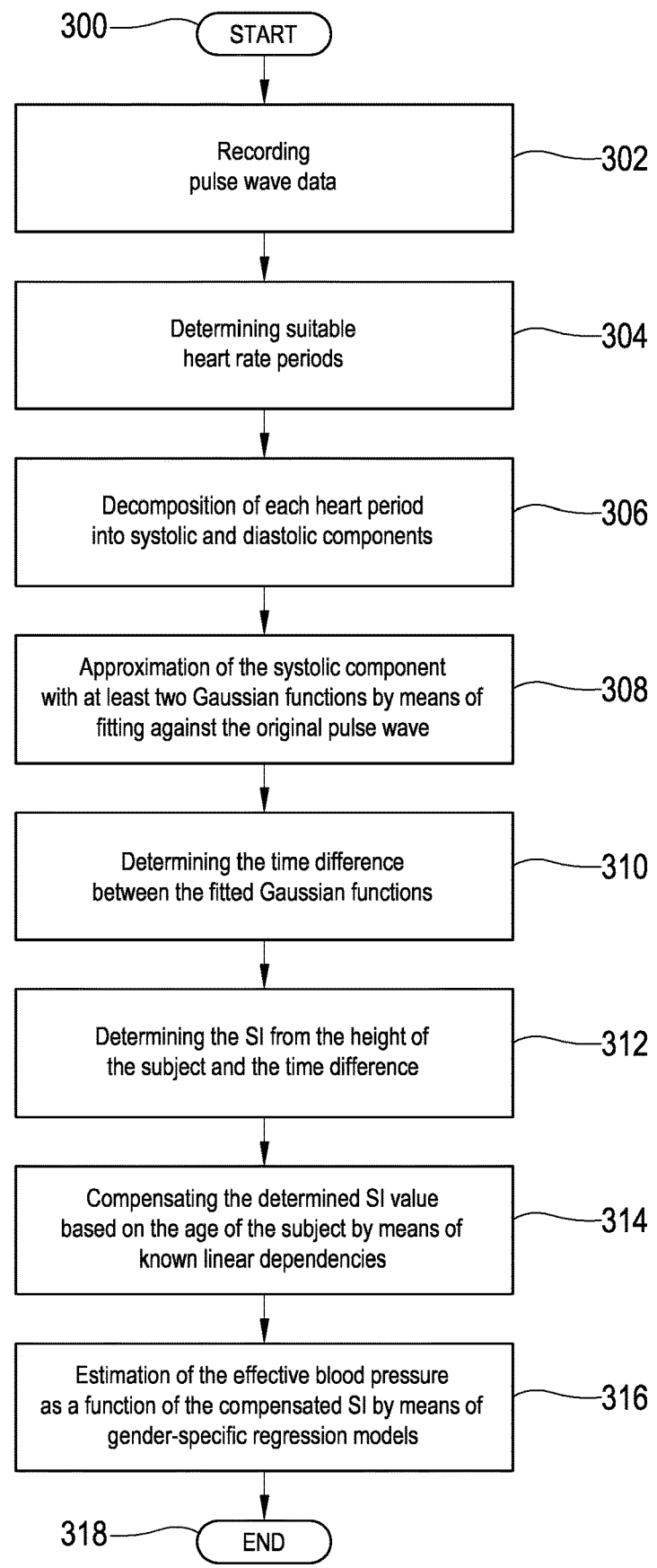
FIG. 3 contains a flow chart of a method for determining blood pressure in accordance with a first embodiment of the invention.

FIG. 3 contains a flow chart of a method 300 for determining blood pressure in accordance with a first embodiment of the invention. In step 302, pulse wave data is recorded. The detection of pulse waves and the recording of data indicative of the detected pulse wave can be performed in any way known in the art. For example, classic photoplethysmography. One example of detection and recording of pulse wave data is described further below with respect to FIG. 4.

In step 304 suitable heart periods are determined. As described above, heart periods vary depending on a number of factors and can exhibit benign (e.g. non-pathological) irregularities, for example caused by stress or anxiety, or consumption of stimulants such as caffeine, nicotine, or alcohol. In order to establish a sound basis for further processing of pulse wave data, suitable heart periods are selected from a longer recording of pule wave data. In the first embodiment, 5 to 30 heart periods are selected from a pulse wave recording of 5 seconds up to 2 minutes in length, provided that all selected heart periods have a similarity to each other of at least 0.8 and are all contained in a single recording segment (i.e. are successive to each other). In other embodiments, a greater or smaller number of successive heart periods may be used, for example 3 to 10 or 20 to 50 heart periods. Further, the recording of pulse wave data can have a different length, for example ranging from 5 to 10 seconds up to 10 to 30 minutes.

In step 306, each heart period is decomposed or partitioned into a systolic and a diastolic component. This is achieved by determining the maximum of the second order derivative of the pulse wave, located at most 350 ms after the systolic maximum. Typically, the maximum of the second order derivative of the pulse wave is located between 250 ms and 350 ms after the systolic maximum. Determining the maximum of the second order derivative is restricted to the above-defined time window in order to take into account the expulsion time of the heart and in order to avoid erroneous detection.

In step 308, an approximation is performed in which the systolic component is approximated by fitting at least two Gaussian functions to the original pulse wave:

$$F(a, b, c, d, f) = \sum_{i=1}^{N} \left( S_i - \left( a \cdot e^{-\frac{1}{2}\left(\frac{t-b}{c}\right)^2} + d \cdot e^{-\frac{1}{2}\left(\frac{t-f}{c}\right)^2} \right) \right)^2 \stackrel{!}{=} \min$$

with a, b, c, d, and f being determined using non-linear optimization. In one embodiment, the two Gaussian functions are fitted to the original pulse wave using the Levenberg-Marquardt algorithm. In this approximation step, the first Gaussian function corresponds to the original pulse wave and the second Gaussian function corresponds to the wave reflected at the aortic bifurcation, whereas the amplitude of the first Gaussian function must be greater or equal to the amplitude of the first Gaussian function, and both functions must exhibit an identical standard deviation a.

In step 310, the time difference between the two Gaussian functions is calculated as the wave-to-wave time WWT. For example, the WWT can be calculated as the time difference between the base points of the two Gaussian functions. Alternatively, the WWT can be calculated as the time difference between the maxima of the two Gaussian functions. In order to generate an overall or averaged $WWT_a$, the median value over 5 to 30 (or any desired number of) heart periods is calculated. This can effectively reduce the impact of outliers.

In step 312, the stiffness index SI is calculated based on the subject height h (in m) and the averaged $WWT_a$ (in s) as:

$$SI = \frac{h}{WWT_a}$$

In step 314, the SI value calculated in step 312 is adjusted in order to compensate for the age of the subject. As described above, the elasticity of a person's vascular system decreases with increasing age, so that the average healthy person at an age of 20 necessarily exhibits a lower SI than the average healthy person at an age of 40 or 60. Therefore, the SI is normalized in step 314 in order to achieve comparable results. In the first embodiment, the SI is normalized in order to obtain an age-independent or adjusted SI.

In step 316, the adjusted SI is estimated based on a gender-specific regression model. The gender-specific regression models are the result of proprietary clinical studies and define the estimated blood pressure of a subject as a function of gender and the adjusted SI. In one example, a male person exhibiting an adjusted SI of 10 may have an estimated systolic blood pressure of 180 mm Hg. Clinical studies were conducted in order to determine how the adjusted SI relates to the actual blood pressure depending on the gender of a subject. It has been found that, with male subjects, an adjusted SI of about 10 m/s corresponds to a blood pressure of about 170 mm Hg, and an adjusted SI of about 8 m/s corresponds to a blood pressure of about 150 mm Hg. With female subjects, an adjusted SI of about 10 m/s corresponds to a blood pressure of about 165 mm Hg, and an adjusted SI of about 8 m/s corresponds to a blood pressure of about 155 mm Hg.

Figure 4:
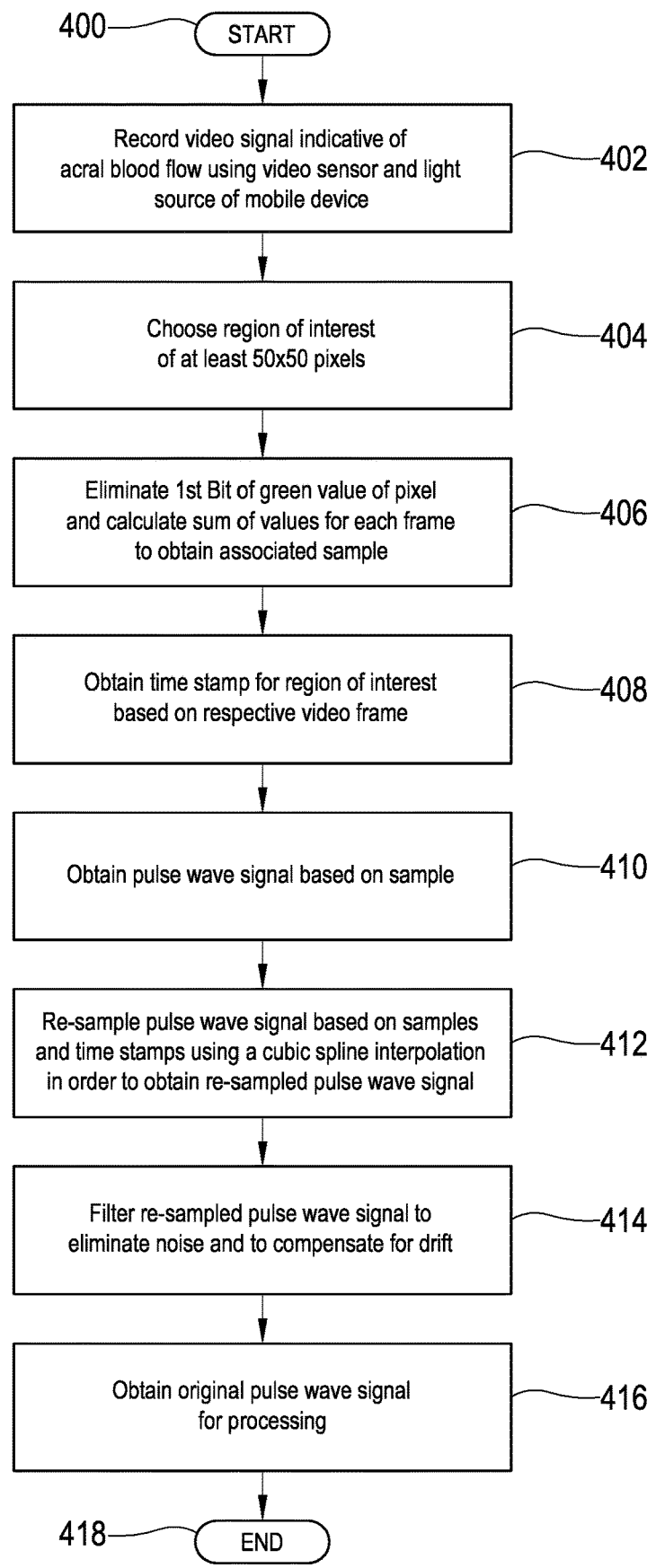
FIG. 4 contains a flow chart of a method for recording pulse wave data in accordance with the present invention, using a mobile device.

FIG. 4 contains a flow chart of a method 400 for recording pulse wave data in accordance with the present invention, using a mobile device having video recording capabilities. Mobile communication devices, in particular so-called smart phones, have extensive capabilities beyond mere telecommunication. For example, most mobile phones are typically provided with a digital camera capable of capturing still images and video and with a corresponding light source for low-light situations. In general, to record a pulse wave by detecting, with an optical sensor, light emitted from a light source and reflected by a finger of a subject. In one embodiment, pulse wave data is obtained using a common mobile device equipped with a digital camera (e.g. used as an optical sensor) and an LED flashlight (e.g. used as a light source). The light emitted by the light source is reflected and the properties of the light (e.g. intensity, hue, brightness, saturation) are affected (e.g. one or more of the properties are modulated) by the acral blood flow.

In step 402, the subject places their finger on both the light source and the camera of the mobile device such that light emitted from the light source illuminates the acral blood flow and is reflected and detected by the camera. The video signal thus created is recorded and stored in a memory unit of the device. Alternatively, the video signal (e.g. a video stream) can be processed directly, without necessitating storing the pulse wave data in a memory unit.

In step 404, a region of interest (ROI) is selected from the full resolution video stream. This selection can be performed, for example, based on brightness information contained in the video stream. In one embodiment, the ROI is determined in a region of maximum brightness within a video frame, off the center and at a minimum distance from the border. This can ensure that a region is chosen that is sufficiently illuminated (e.g. a region close to the light source). In one embodiment, the ROI has a size of at least 50×50 pixels (i.e. 2500 square pixels). Generally, the ROI can have a size ranging from 625 to 10000 square pixels, preferably 900 to 6400 square pixels, more preferably 1600 to 3200 square pixels.

In step 406, for the ROI of each frame of the video stream, a sample $s_i$ is calculated, based on $$s_i = \sum_{j=0}^{N-1} \sum_{k=0}^{M-1} \frac{p(j \cdot w + k)}{2}$$

with p being the value of the green channel of the pixel located within the ROI at the position j,k; N and M being the size of the ROI; and w being the width of the ROI. The division by 2 eliminates the lowest Bit of p, such that noise is effectively reduced. This produces a sample $s_i$ for each captured video frame.

In step 408, a time stamp $t_i$ is generated for each sample $s_i$ (more accurately, for each video frame, based on which the sample was calculated) and encoded into the video stream by the video camera.

In step 410, the pulse wave is obtained as a pulse wave signal based on the samples $s_i$ obtained in step 406.

In step 412, a re-sampled pulse wave is obtained by re-sampling the pulse wave from the samples $s_i$ (i.e. as obtained in step 410) based on the associated time stamps obtained in step 408. This is necessary due to technical issues in detecting, generating, and encoding video data, for example resulting in dropped frames or non-constant frame rates. Based on these issues, the samples $s_i$ cannot be obtained at fixed and reliable time intervals. In order to obtain the re-sampled pulse wave, the pulse wave is re-sampled using a cubic spline interpolation and is performed on each polynomial. Here, two subsequent samples are interpolated by a third-degree polynomial. The position (in time) of the samples corresponds to the time stamps. The polynomial $S_i$ for the range $[t_i, t_{i+1}]$ is calculated as follows:

$$S_i = a_i + b_i(t-t_i)^2 + d_i(t-t_i)^3$$

with i=1, . . . , n-1. The process of re-sampling includes incrementing t continuously by 1 ms, corresponding to a sample rate of 1000 Hz. The parameters $a_i$, $b_i$, $c_i$, and $d_i$ have to be set to suitable values. The pulse wave is obtained as the signal S being the result of the re-sampling.

In step 414, the re-sampled pulse wave is filtered to eliminate noise and to compensate for drift. This can be achieved by applying a common bandpass filter (e.g. 0.1 to 10 Hz).

In step 416, the original pulse wave signal is obtained in order to be processed further, as described above with respect to FIG. 3 (see, e.g., steps 304 ff.)

Figure 5A:
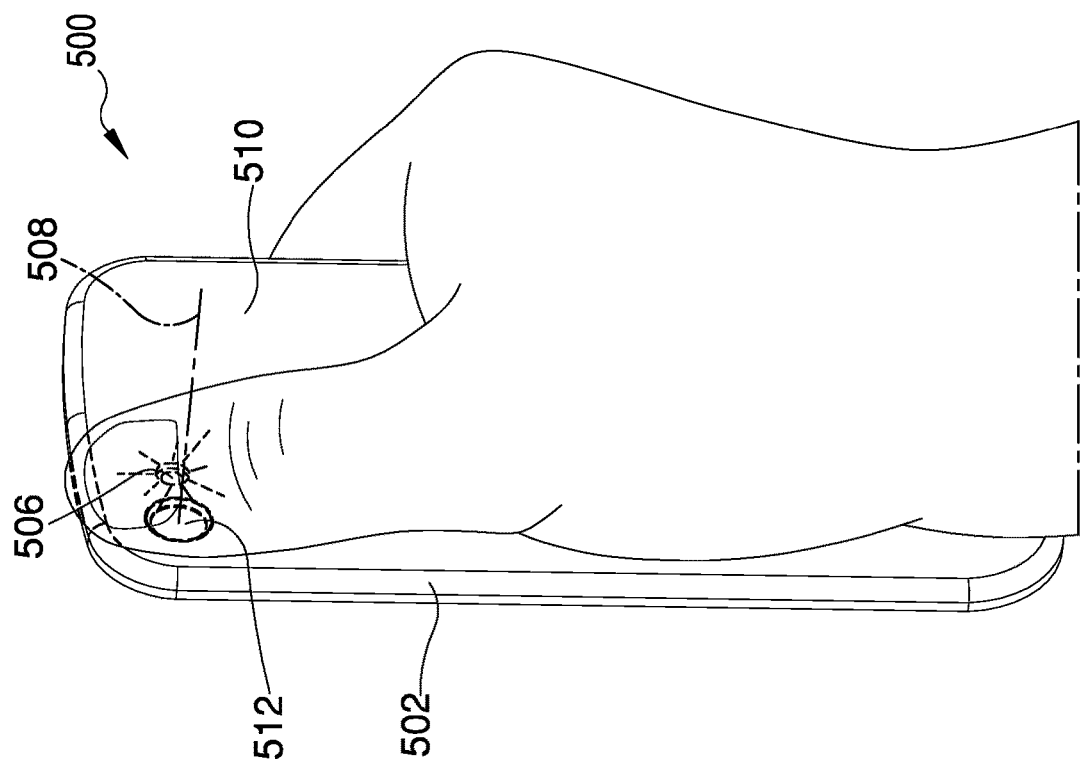
FIG. 5A illustrates an interaction of a human subject with the mobile device shown in FIG. 5.
Figure 5:
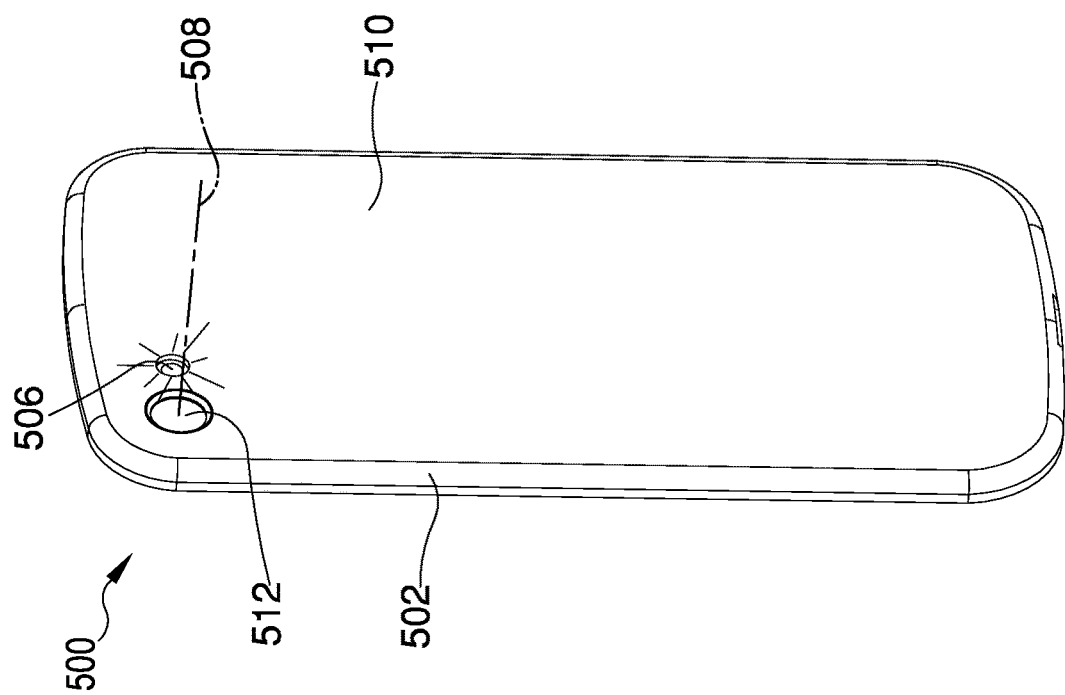
FIG. 5 illustrates an exemplary mobile device that can be used in accordance with the method of FIG. 4.

FIG. 5 illustrates a exemplary mobile device that can be used in accordance with the method of FIG. 4. The mobile device 500 has a frame or main body 502 and a device panel 510. In some examples, the device panel 510 can be a back panel of the mobile device 500. The device 500 further has a camera device 512 capable of detecting digital video signals, for example in the form of digital still images and digital video. The camera device 512 is configured to detect video signals representative of objects located generally with a frustum-shaped region along a main detection direction 508. The device 500 further has a light source 506 configured to illuminate any objects located in front of camera device 512, i.e. located within the frustum-shaped region and/or along a main detection direction 508. The light source 506 can be configured to provide both a single flash of light and a continuous light beam, depending on a mode of operation. When recording video, the light source typically provides a continuous light beam. Light emitted from light source 506 will be reflected by an object placed within the view of camera device 512 so that the reflected light can be detected by camera device 512. Mobile device 500 further comprises a control unit (e.g. a CPU, micro processor, SoC; not shown) coupled to other components, such as camera device 512, light source 506, a memory unit, a user interface, input means, an audio unit, a video unit, a display, and other.

FIG. 5A illustrates an interaction of a human subject with the mobile device shown in FIG. 5. In order to take a measurement, the subject places a finger (e.g. a thumb) on mobile device 500, covering both the camera device 512 and the light source 506. The individual configuration of the mobile device (e.g. a position of camera device 512 and light source 506 or the distance in between) is of secondary relevance, as long as it is physically possible to cover both the camera device 512 and the light source 506 with a suitable extremity (e.g. finger, thumb, ear). In this respect, any extremity suitable for (acral) measurement can be used in accordance with the present invention. In general, any body part that is associated with pulsating blood flow can be used in accordance with the present invention, as long as a meaningful signal indicative of the blood flow can be detected via the body part. In some embodiments, the control unit of mobile device 500 will process signals provided by camera device 512 and detect, based on the signals provided, that one or more parameters indicative of video quality (e.g. brightness, contrast, focus) are outside of preferred operating ranges due to the low-light and/or close-proximity situation created by the placement of the thumb directly onto camera device 512. The control unit may then provide control signals to one or more components, for example to light source 506, in order to make adjustments to the parameters (e.g. activating light source 506 in order to compensate for low light).

Upon placement of the suitable extremity (here, e.g., the thumb of the subject), the measurement is initiated by activating the light source 506 to emit a continuous light beam of sufficient intensity, such that acral blood flow is illuminated. At substantially the same time, camera device 512 is activated and the light reflected by the acral blood flow is detected by camera device 512. Both activating the light source 506 and activating the camera device 512 can be achieved by corresponding program code executed by the control unit comprised in device 500. The activation can be triggered manually, for example by selecting a corresponding function on a user interface of device 500, or automatically, for example triggered by a sensor (e.g. a proximity sensor, an optical sensor), a timer, voice recognition, or other (input means). In one example, the signal of the sensor is continuously processed to check for the presence of a suitable signal. Video data is then recorded or transmitted for further processing for a predetermined period of time, typically ranging from several seconds to 2 minutes. In some embodiments, the time period is not predetermined, but determined as the recording/transmitting is ongoing, in that a quality measure is calculated from the recorded/transmitted data and the recording/transmitting is performed until a sufficient number of heart periods (e.g. 10-30) of sufficient quality (e.g. similarity; see in further detail below) has been recorded/transmitted. Completion of the recording/transmitting can be indicated to the subject, for example, by an acoustic and/or optical signal emitted by an audio and/or video component of device 500.

Figure 6:
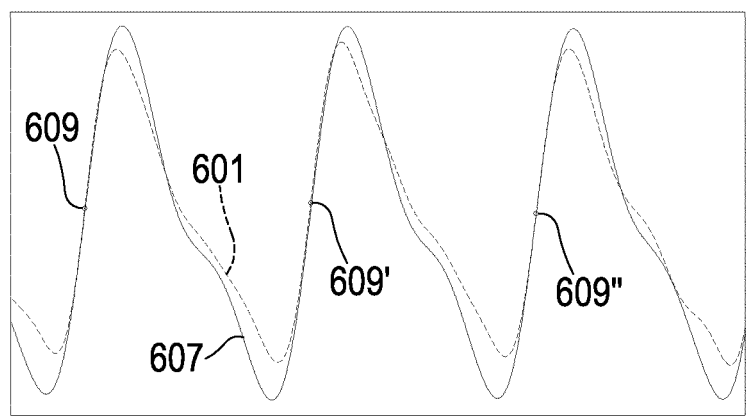
FIG. 6 illustrates how a series of heart periods is determined based on acquired pulse wave data.

FIG. 6 illustrates how a series of heart periods is determined based on acquired pulse wave data 601. Pulse wave data can be acquired from live measurements taken with a human subject or can be retrieved from data storage when measurements recorded at an earlier time are to be processed. Pulse wave data 601 contains signals corresponding to a number of heart periods exhibited by the subject over an extended time period. In some examples, the pulse wave data cover several minutes of recorded heart periods, for example 2 minutes, preferably several seconds to 2 minutes. In other examples, the pulse wave data can cover substantially less (e.g. 5-30 seconds) or more (several hours) of recorded heart periods. For reasons of clarity, FIG. 6 shows merely three successive heart periods representing only a small window of pulse wave data covering an extended period of time of typically up to 2 minutes.

The pulse wave data 601 is partitioned into single heart periods by generating an amplified wanted signal 607 from the original pulse wave 601 and scanning the amplified signal for rising edges. In general, a pulse wave comprising a single heart period is sufficient, but typically a pulse wave comprising a plurality of successive heart periods is used. In detail, a spectrum is created from the filtered (see FIG. 4, step 414, and corresponding description above) pulse wave signal 601 using discrete Fourier transformation (DFT): Spec=|DFT($S_{filter}$)|. In this spectrum, the maximum frequency in the range of 0.6 Hz to 2.5 Hz is determined and regarded as the dominant heart frequency: idx=argmax{$Spec_{range}$}, wherein $Spec_{range}$ corresponds to the spectrum from 0.6 Hz to 2.5 Hz and idx corresponds to the index (i.e. frequency) in the spectrum. Then, a normalized Gaussian graph having values in the range [0,1] is superposed over the dominant heart frequency and over the 2 harmonic components thereof, such that a minor variation of the heart rate is accounted for. The standard deviation σ of the Gaussian graphs should intersect at 3σ, with:

$$\sigma = \frac{idx}{6} \text{ and gauss}(t) = e^{-\frac{1}{2}\left(\frac{t-idx}{\sigma}\right)^2} + e^{-\frac{1}{2}\left(\frac{t-2 \cdot idx}{\sigma}\right)^2} + e^{-\frac{1}{2}\left(\frac{t-3 \cdot idx}{\sigma}\right)^2}.$$

The wanted signal is obtained by multiplying the spectrum with the Gaussian function and subsequent back transformation: $S_{wanted}$=Real(|DFT(Spec·gauss)). The amplified signal $S_{amp}$ is then obtained by multiplication of the wanted signal and addition to the original signal:

$$S_{amp} = \frac{1}{2}\left(\frac{S_{filter}}{f} + f \cdot S_{nutz}\right),$$

with f being the amplification factor. Subsequently, the first order derivative of the amplified signal $S_{amp}$ is calculated and the maxima thereof, indicating the inflection points on the amplified signal $S_{amp}$, and, thus, the rising edges thereof. This provides the location of each heart period, defined between the two local minima before and after the rising edge of each heart period.

For a successive number of heart periods, a similarity score is then determined. A cross correlation of each heart period with a template heart period $P_{template}$ is calculated and a predetermined number of heart periods (e.g. 10 heart periods) having the highest correlation is obtained. In one embodiment, the similarity (i.e. correlation) of successive heart periods is 0.9 or greater. If each heart period of a minimum number of successive heart periods (e.g. 10-30) fulfills the similarity requirement, then a portion of the pulse wave suitable for further processing has been identified.

Figure 7:
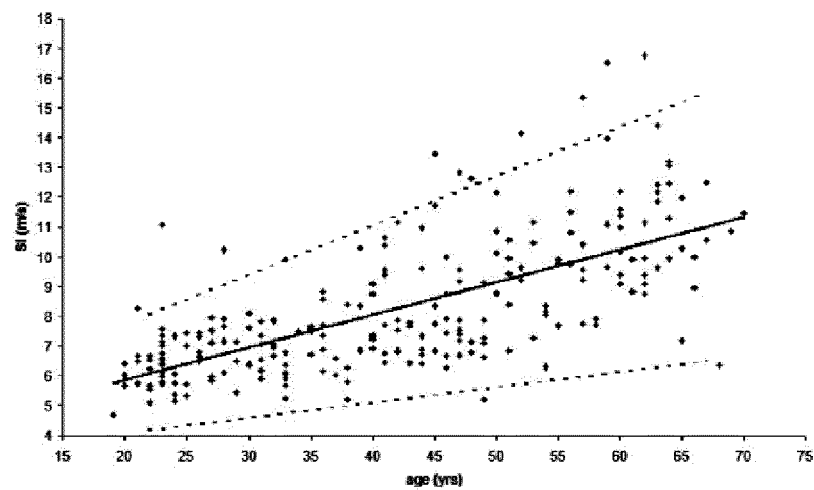
FIG. 7 illustrates how an exemplary adjustment function for adjusting the stiffness index to the age of a subject is determined.

FIG. 7 illustrates how an exemplary adjustment function for adjusting the stiffness index to the age of a subject is determined. The horizontal axis of the graph indicates the age of a subject (in years) and the vertical axis indicates the SI (in m/s). The distribution of measured SI of a number of subjects and a correlation with the age of the respective subject provides a statistical basis for computing the adjustment function as shown in FIG. 7. Here, the SI of a subject being 60 or 65 years of age can be correlated to the SI of a subject being 20 or 25 years of age.

Figure 8:
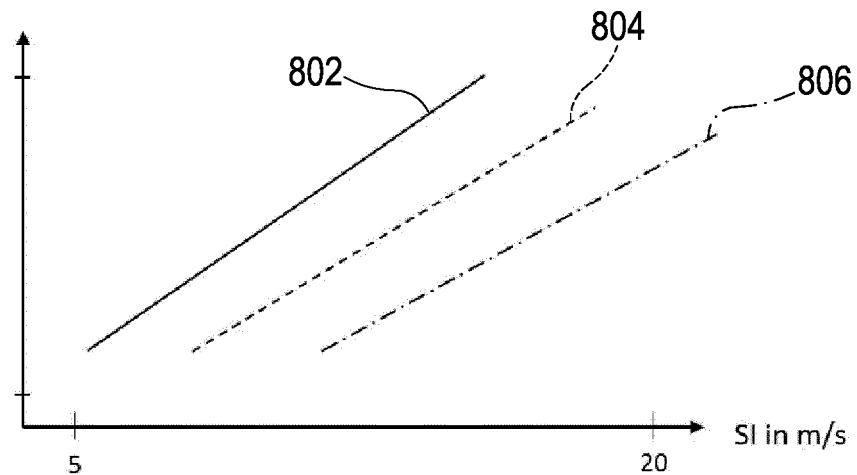
FIG. 8 illustrates how an exemplary regression model for determining the blood pressure of a subject based on the adjusted stiffness index is determined.

FIG. 8 illustrates how an exemplary regression model for determining the blood pressure of a subject based on the adjusted stiffness index is determined. The regression model is age-dependent in that regression line 802 serves to provide a regression function for subjects aged 20 to 30 years. In the same manner, regression lines 804 and 806 serve to provide regression functions respectively for subjects aged 30 to 40 years and 60 to 70 years. The regression model facilitates associating the SI of a subject belonging to a particular age group to a corresponding blood pressure value. As the data underlying the regression model is updated, the regression model can be adjusted over time in order to improve the accuracy thereof.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for determining blood pressure, comprising:
a memory to store program code;
a processor coupled to the memory and configured to execute the program code having instructions which, when executed by the processor, cause the processor to perform operations, the operations comprising:
receiving pulse wave data, wherein the pulse wave data defines a heartbeat of a human subject, and wherein the subject is associated with a body height value, an age value, and a gender type;
selecting a portion of the pulse wave data indicative of one or more heart periods;
determining a time difference (WWT) for at least one respective heart period of the one or more heart periods, wherein determining the WWT for the at least one respective heart period comprises:
determining a systolic component of the respective heart period, wherein determining the systolic component comprises:
determining a respective global maximum of the respective heart period;
determining a second order derivative of the respective heart period;
determining a maximum value of the second order derivative located at least at a predetermined time difference from the global maximum; and
defining the systolic component as a portion of the heart period between the start of the heart period and the maximum value;
approximating the systolic component with a first Gaussian function and a second Gaussian function, wherein the first and second Gaussian functions have respective first and second standard deviations ($\sigma_1$, $\sigma_2$), the first and second standard deviations ($\sigma_1$, $\sigma_2$) being equal to each other; and
determining the WWT as the time difference between the first and second Gaussian functions; and
determining a blood pressure value (BP) of the subject based on the WWT, the body height value, and the age value, wherein determining the BP comprises:
determining a preliminary stiffness index ($SI_p$) based on the body height value and the WWT;
determining an adjusted stiffness index ($SI_a$) based on the preliminary stiffness index ($SI_p$) and the age value, wherein the $SI_a$ is determined by adjusting the $SI_p$ according to an adjustment factor including the age value of the subject; and
determining the BP based on the adjusted stiffness index ($SI_a$) and a regression model, wherein the regression model comprises a regression function $f(SI_a, g) = BP_{sys}$, where $SI_a$ is the adjusted stiffness index ($SI_a$), g is the gender type of the subject, and $BP_{sys}$ is the blood pressure;
wherein determining the BP comprises determining the blood pressure value based on the regression function; and
wherein the regression function comprises a linear function of the type $f(x) = ax + b$, where a ranges from 1 to 20 mmHg/(m/s) and b ranges from 0 to 80 mmHg; and
a display comprising a user interface, the display providing the determined BP of the subject for display at the user interface, the display commutatively coupled with the processor.

2. The apparatus according to claim 1, wherein the portion of the pulse wave data is indicative of a plurality of successive heart periods, and wherein determining the time difference (WWT) further comprises:
determining the time difference (WWT) for the plurality of successive heart periods as an average value based on the respective time differences determined for the heart periods of the plurality of heart periods.

3. The apparatus according to claim 1, wherein the first and second Gaussian functions have a respective maximum amplitude, the maximum amplitude of the first Gaussian function being greater than or equal to the maximum amplitude of the second Gaussian function.

4. The apparatus according to claim 1, wherein approximating the systolic component comprises:
fitting the first and second Gaussian functions to the systolic component using $$F(a,b,c,d,f) = \sum_{i=1}^{N} \left( S_i - \left( a \cdot e^{-\frac{1}{2}\left(\frac{t-b}{c}\right)^2} + d \cdot e^{-\frac{1}{2}\left(\frac{t-f}{c}\right)^2} \right) \right)^2 \overset{!}{=} \min$$

with a, b, c, d, and f being determined using non-linear optimization or curve-fitting.

5. The apparatus according to claim 1, wherein determining the adjusted stiffness index ($SI_a$) is based on an adjustment function $f(SI_p) = SI_a$, where $SI_p$ is the preliminary stiffness index and $SI_a$ is the adjusted stiffness index ($SI_a$).

6. The apparatus according to claim 5, wherein the adjustment function is a linear function of the type $f(x) = cx + d$, where c and d are adjustment factors determined based on a plurality of value pairs comprising the age value and an associated stiffness index value.

7. The apparatus according to claim 1, wherein determining the preliminary stiffness index ($SI_p$) is based on a function $$SI_p = \frac{h}{WWT},$$

where h is the body height value, WWT is the time difference, and $SI_p$ is the preliminary stiffness index ($SI_p$).

8. The apparatus according to claim 1, further comprising:
a light source configured to transmit light into an extremity of the subject; and
an optical sensor configured to receive light reflected from blood flow through the extremity.

9. The apparatus according to claim 1, wherein the portion of the pulse wave data is indicative of 1 to 50 heart periods.

10. The apparatus according to claim 1, further comprising an optical sensor and a light source, the optical sensor being configured to detect a signal emitted by the light source and reflected by part of the body of the subject.

11. The apparatus according to claim 1, further comprising:
- a light source configured to transmit light into an extremity of the subject; and
- an optical sensor configured for receiving light reflected from blood flow through the extremity; and further comprising instructions, which when executed by the processor, cause the processor to perform operations including receiving the pulse wave data by activating the light source and receiving the pulse wave data based on a signal provided by the optical sensor.

12. The apparatus according to claim 1, wherein a ranges from 5 to 15 mmHg/(m/s) and b ranges from 20 to 60 mmHg.

13. The apparatus according to claim 2, wherein the average value is the median value of the determined respective time differences.

14. The apparatus according to claim 6, wherein:

$$c = \frac{SI - \mu}{\text{range(age)}}$$

with $\mu=0.109*\text{age}+3.699$ and $\text{range(age)}=0.1663*\text{age}+4.3858-\mu$, age being the age of the subject, and $d=0$.

15. The apparatus according to claim 1, wherein the predetermined time difference from the global maximum is 350 ms or less.

16. The apparatus according to claim 8, wherein the instructions, which when executed by the processor, further cause the processor to perform operations including receiving the pulse wave data by activating the light source and receiving the pulse wave data based on a signal provided by the optical sensor.

17. The apparatus according to claim 8, wherein the optical sensor comprises a video sensor, and wherein receiving the pulse wave data further comprises:

receiving a video stream indicative of the reflected light based on the signal; and selecting a region of interest from the video stream containing a plurality of pixels.

18. The apparatus according to claim 17, wherein the region of interest has a size of 50×50 pixels.

19. The apparatus according to claim 17, further comprising instructions which when executed by the processor cause the processor to perform operations, the operations comprising:

selecting a plurality of frames from the video stream, each frame of the plurality of frames having a respective time stamp; and for each respective frame:
- determining, within the region of interest, a first sample value indicative of the sum of the values of a green subcomponent of each pixel of the plurality of pixels;
- associating each first sample value with the respective time stamp;
- generating a first pulse wave from the first sample value; and
- determining a second pulse wave by re-sampling the first pulse wave based on the respective time stamps.

20. The apparatus according to claim 19, wherein determining the second pulse wave further comprises filtering the second pulse wave using a bandpass filter.

21. The apparatus according to claim 20, wherein the bandpass filter removes all frequencies not falling within a range from 0.6 Hz to 2.5 Hz.

22. The apparatus according to claim 9, wherein the portion of the pulse wave data is indicative of a plurality of successive heart periods.

23. The apparatus according to claim 10, wherein the part of the body of the subject comprises a pulsatile blood flow of the subject.

* * * * *